(12) United States Patent
Dogariu et al.

(10) Patent No.: US 7,551,289 B2
(45) Date of Patent: Jun. 23, 2009

(54) SIGNAL ANALYSIS USING MULTI-MODE, COMMON-PATH INTERFEROMETRY

(75) Inventors: Aristide Dogariu, Winter Springs, FL (US); Erwan Baleine, Orlando, FL (US)

(73) Assignee: University of Central Florida Research Foundation, Orlando, FL (US)

( * ) Notice: Subject to any disclaimer, the term of this patent is extended or adjusted under 35 U.S.C. 154(b) by 169 days.

(21) Appl. No.: 11/399,632

(22) Filed: Apr. 6, 2006

(65) Prior Publication Data

US 2007/0236698 A1 Oct. 11, 2007

(51) Int. Cl.
*G01B 9/02* (2006.01)
(52) U.S. Cl. ...................................... 356/479
(58) Field of Classification Search ................ 356/479, 356/497, 477, 478, 480, 481, 482, 521
See application file for complete search history.

(56) References Cited

U.S. PATENT DOCUMENTS

| | | | | |
|---|---|---|---|---|
| 5,555,087 | A * | 9/1996 | Miyagawa et al. | 356/485 |
| 5,710,630 | A | 1/1998 | Essenpreis et al. | 356/345 |
| 5,991,697 | A | 11/1999 | Nelson et al. | 702/49 |
| 6,525,823 | B1 | 2/2003 | Dogariu et al. | 356/479 |
| 6,943,892 | B2 * | 9/2005 | Chan | 356/479 |
| 6,958,816 | B1 | 10/2005 | Dogariu et al. | 356/479 |
| 2006/0114473 | A1 * | 6/2006 | Tearney et al. | 356/479 |

OTHER PUBLICATIONS

Popescu, et al.; "Spatially resolved microrheology using localized coherence volumes", published Apr. 3, 2002.
Pepescu, et al; "Dynamic light scattering in localized coherence volumes", published Oct. 20, 2000; pp. 551-553.
Mason, et al. "Optical Measurements of Frequency-Dependent Linear Viscoelastic Moduli of Complex Fluids," Physical Review Letters, The American Physical Society, vol. 74, No. 7, Feb. 13, 1995, pp. 1250-1253.
Gittes, et al. "Microscopic Viscoelasticity: Shear Modui of Soft Materials Determined from Thermal Fluctuations," Physical Review Letters, The American Physical Society, Oct. 27, 1997, pp. 3286-3289.

(Continued)

*Primary Examiner*—Hwa (Andrew) S Lee
(74) *Attorney, Agent, or Firm*—Thomas, Kayden, Horstemeyer & Risley, LLP

(57) ABSTRACT

A light scattering sensing system and method. In one embodiment, the system includes a sample branch configured to collect light signals backscattered from scattering centers contained in a coherence volume of a medium under evaluation, the sample branch including a multi-mode optical waveguide. In one embodiment, the method includes radiating low-coherence light into a scattering medium using a multi-mode optical waveguide, and collecting light signals backscattered by the scattering centers and light reflected by an end surface of the multi-mode optical waveguide using the multi-mode optical waveguide.

18 Claims, 6 Drawing Sheets

OTHER PUBLICATIONS

Levine, et al. "One-and Two-Particle Microrheology," Physical Review Letters, vol. 85, No. 8, The American Physical Society, Aug. 21, 2000, pp. 1774-1777.

Bizheva, et al. "Path-Length-Resolved Dynamic Light Scattering in Highly Scattering Random Media: The Transition to Diffusing Wave Spectroscopy," Physical Review E, The American Physical Society, vol. 58, No. 6, Dec. 1998, pp. 7664-7667.

Popescu, et al. "Evidence of Scattering Anisotropy Effects on Boundary Conditions of the Diffusion Equation," Physical Review E, vol. 61, No. 4, Apr. 2000, pp. 4523-4529.

Popescu, et al. "Optical Path-Length Spectroscopy of Wave Propagation in Random Media," Optics Letters, 1999 Optical Society of America, vol. 24, No. 7, Apr. 1, 1999, pp. 442-444.

Mackintosh, et al. "Microrheology," Current Opinion in Colloid & Interface Science 4 (1999), Elsevier Science Ltd, pp. 300-307.

* cited by examiner

SIGNAL ANALYSIS USING MULTI-MODE, COMMON-PATH INTERFEROMETRY

BACKGROUND

The rheological properties of fluids are complex and controlled by many parameters. For example, biological fluids, such as blood, are viscoelastic, i.e., they exhibit both viscosity and elasticity.

A number of techniques have been developed or suggested for evaluating the rheological properties of fluids on a microscopic scale. This area of science has become known as microrheology. Several microrheological techniques rely on applying a strain to the fluid through application of an external force, such as a mechanical force or a magnetic field. Such techniques may be undesirable, however, because the fluid under evaluation is evaluated under artificial conditions.

In a more recent approach described in U.S. Pat. No. 6,958,816, microrheological properties of a fluid are observed through low-coherence light scattering. In such analysis, a very small volume of the fluid under evaluation is observed by collecting backscattered rays that are reflected from scattering centers suspended in the volume when light is radiated into the fluid via a single-mode optical fiber. Such an arrangement is depicted in FIG. 1. As is indicated in that figure, light transmitted through the core 100 of a single-mode optical fiber 102 is reflected (arrow A) by scattering centers 104 suspended in a fluid under evaluation 106, and reflected (arrow B) by the end surface 108 of the single-mode optical fiber core. In such an approach, a very small volume 110, e.g., a tenth of a picoliter, of the fluid under evaluation 106 is observed, in part due to the small cross-sectional area of the single-mode optical fiber core 100. Such observation of a very small volume of fluid has been considered preferable given that the received optical signals can become very complex, and therefore difficult to evaluate, when a high concentration of scattering centers are observed due to multiple ray scattering that occurs between the scattering centers.

Although the light scattering approach described above has significant advantages over previous techniques, the signal-to-noise ratio for the received signals is relatively small given that the number of scattering centers from which reflected light is collected is relatively small.

SUMMARY

Disclosed is a light scattering sensing system and method. In one embodiment, the system comprises a sample branch configured to collect light signals backscattered from scattering centers contained in a coherence volume of a medium under evaluation, the sample branch comprising a multi-mode optical waveguide. In one embodiment, the method comprises radiating low-coherence light into a scattering medium using a multi-mode optical waveguide, and collecting light signals backscattered by the scattering centers and light reflected by an end surface of the multi-mode optical waveguide using the multi-mode optical waveguide.

BRIEF DESCRIPTION OF THE FIGURES

The components in the drawings are not necessarily to scale, emphasis instead being placed upon clearly illustrating the principles of the present disclosure. In the drawings, like reference numerals designate corresponding parts throughout the several views.

DETAILED DESCRIPTION

Figure 1:
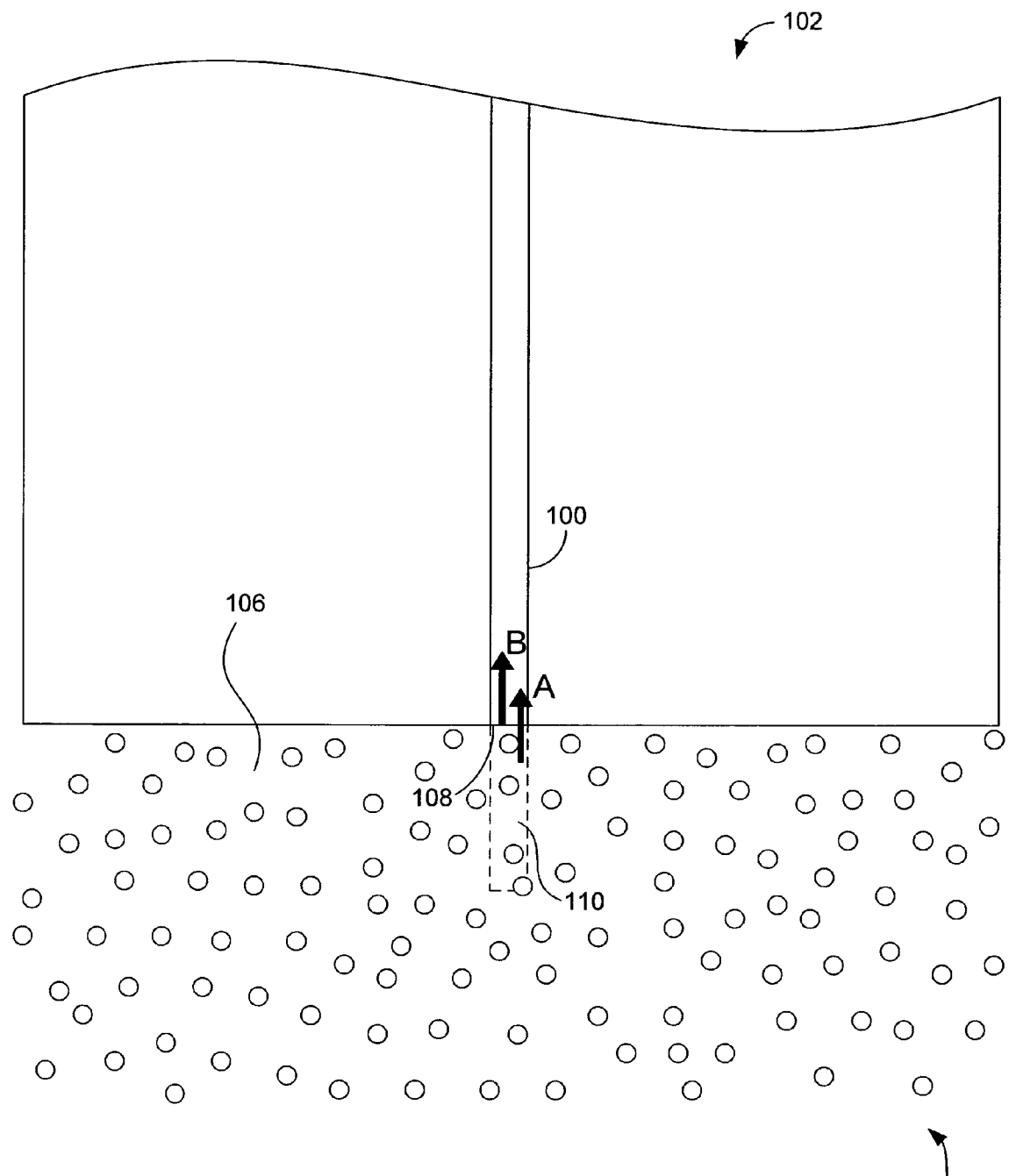
FIG. 1 illustrates a prior art method for collecting light signals using a single-mode optical fiber.

As described above, the microrheological properties of a fluid can be observed by collecting backscattered rays that are reflected from scattering centers suspended in the fluid when light is radiated into the fluid via a single-mode optical fiber. In such an approach, a very small volume of the fluid under evaluation is observed, in part due to the small cross-sectional area of the single-mode optical fiber core. Observation of a very small volume of fluid has been considered preferable given that the received optical signals can become very complex, and therefore difficult to evaluate, when a high concentration of scattering centers is observed due to multiple ray scattering that occurs between the scattering centers. Specifically, rays resulting from multiple inter-reflection between individual scattering centers can unduly complicate the received signals and therefore analysis of the fluid. Therefore, increasing the depth of the observed volume (see volume 110, FIG. 1) volume is undesirable.

Although the effects of such multiple scattering are reduced when a very small volume of fluid is evaluated in the manner described in the foregoing, the signal-to-noise ratio of the received signals is relatively low. That is, because a very small volume of fluid is observed, reflected light is only collected from a relatively small number of scattering centers. Given that the few observed scattering centers are used as probes that are indicative of the microrheological properties of the fluid as a whole, it would be preferable to obtain reflected light signals from a greater number of scattering centers, without a significant increase in multiple-scattered signals.

As is described in the following, light can be collected from a greater number of scattering centers when multi-mode optical waveguides are used due to the larger cross-sectional area of the cores of such multi-mode optical waveguides. As a result, the signal-to-noise ratio is increased due to greater collection efficiency. However, because the depth of the observed volume is not increased, multiple scattering is not significantly increased even for optically dense suspensions.

Before describing the disclosed embodiments in detail it is noted that the invention is not limited in its application to the details of those particular embodiments since the disclosed systems and methods are capable of other embodiments. Also, the terminology used herein is for the purpose of description and is not intended to limit the disclosure.

In the techniques described herein, light backscattered from scattering centers suspended within from a small volume of media localized at the end of an optical waveguide is collected. The collected light is detected and analyzed, for example in the frequency domain. Owing to the refractive index contrast between the fiber core and the medium in which the scattering centers are suspended, the signal that is detected has two components: (i) the light that is backscattered from the dynamic system, and (ii) the component that is due to the Fresnel reflection at the fiber-medium interface. The coherence length and the transverse dimension of the fiber core define a coherence volume in which the optical fields preserve relative phase correlations. Considering the terms that survive the time averaging, we were able to derive the expression for the intensity autocorrelation function as $$G^2(\tau) = I_0^2 + 2I_0 I_s + I_s^2 + \quad \text{[Equation 1]}$$
$$I_0 \sum_j I_j [g_j(\tau) + g_j(\tau)^*] \times \exp[-2(s_j - s_0)^2 / l_c^2] +$$
$$\sum_{k \neq l} I_k I_{gk}(\tau) g_l(\tau)^* \times \exp[-2(s_k - s_l)^2 / l_c^2]$$

In Equation 1, $I_0$ and $I_s = \Sigma_j I_j$ are the average intesities of the specular and the scattered components, respectively, and $I_j$ is the intensity associated with the backscattered component of trajectory j. The term $g_j$ represents the normalized first-order correlation function corresponding to the backscattered component, defined as $g_j(\tau) = \langle E_j(\tau) E_j(t+\tau)^* \rangle / I_j$, with the angle brackets denoting time averaging and the symbol * representing complex conjugation. The optical path lengths associated with the scattered component j and the specular field are denoted $s_j$ and $s_0$, respectively, and $l_c$ is the coherence length. An important consequence of Equation 1 is that for scattering media with the mean free paths longer than $l_c/2$, the backscattered light undergoes on average only one scattering event in the coherence volume, which is defined approximately by the coherence length and the area of the fiber core. Consequently, the autocorrelation functions $g_j$ are independent of the length of the scattering trajectory and are given by the well-established formula for quasi-elastic light scatter. If $I_s << I_0$, the last (self-beating) term of Equation 1 becomes negligible. With these assumptions, Equation 1 can be arranged to give the normalized autocorreclation function $$g^{(2)}(\tau) = 1 + 2 \frac{I_0 I_s^{CV}}{(I_0 + I_s^{CV})^2} g_{(r)}^{(l)} \quad \text{[Equation 2]}$$

In Equation 2, $g^{(1)}(\tau) = \exp(-q^2 D\tau)$, where D is the particle diffusion coefficient and q is the scattering vector, which, for our backscattering geometry, equals twice the wave number $(4\pi/\lambda)$. For Brownian particles of diameter d, the diffusion coefficient relates to the temperature T and the viscosity $\eta$ of the medium through the well-known Stokes-Einstein expression $D = k_B T / 3\pi\eta d$, where $k_B$ is Boltzmann's constant. The quantity $I_s^{CV}$ in Equation 2 represents the average intensity of the light scattered from the coherence volume, $I_s^{CV} = \Sigma_j I_j \exp[-2(s_j - s_0)^2 / l_c^2]$. For all the real light sources, the coherence length has a finite value, and therefore the inequality $I_s^{CV} < I_s$ always applies.

The investigated media can be optically dense but can still be analyzed by a single scattering model, as described in Equation 2. The fluctuations of the scattered light have been analyzed in the frequency domain based on the Fourier-transform relationship between the intensity autocorrelation function $G^2(\tau)$ and the power spectrum $P(\omega)$. The associated power spectrum has a Lorentzian shape, $$P(\omega) = \frac{A_0}{\Omega} \frac{1}{1 + (\omega/\Omega)^2} \quad \text{[Equation 3]}$$

where $\Omega = D_q^2$ and $A_0$ is the spectrum amplitude proportional to the product $I_0 I_s^{CV}$. Thus the amplitude $A_0$ of the power spectrum can be expressed in simple form as $A_0 = \alpha \rho Q_b / d$ where d is the diameter of the particle, $Q_b$ is the backscattering efficiency, $\rho$ is the density of the particles by volume, and $\alpha$ is an experimental constant. Since the dimension of the particle can be determined from the width of the power spectrum, as described above, the backscattering efficiency $Q_b$ can be calculated for particles with known optical properties. Consequently, the particle concentration is obtained by the measurement of the $A_0$ and calibration for the experimental constant, $\alpha$.

Figure 2:
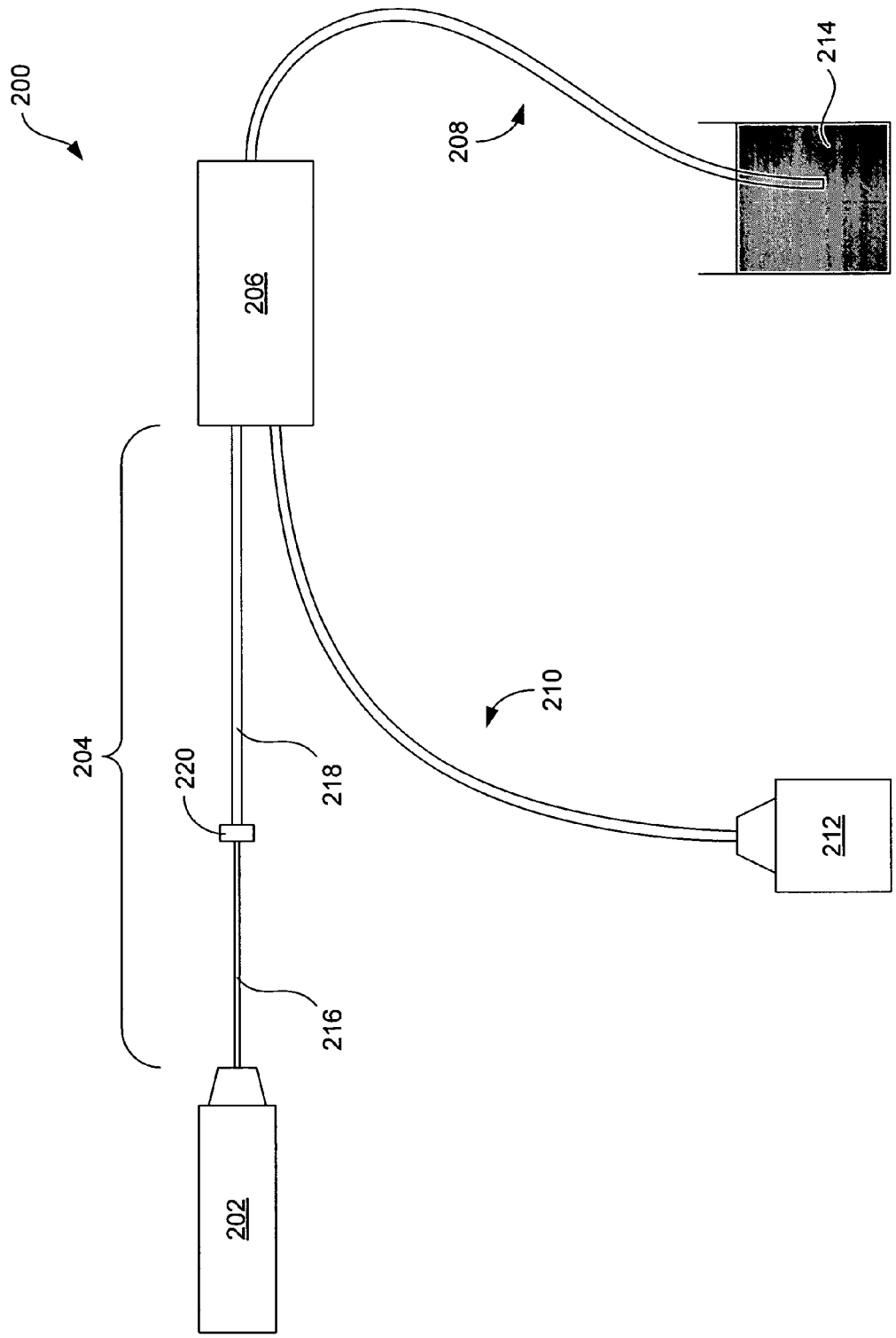
FIG. 2 illustrates a first embodiment of a light scattering sensing system.

FIG. 2 illustrates an embodiment of a light scattering sensing system 200 that can be used to collect light scattered by particles in a given medium. The system 200 is configured as a multi-mode, common-path interferometer that includes a light source 202, a source branch 204, an optic coupler 206, a sample branch 208, a detector branch 210, and a detector 212. The light source 202 emits light that is delivered to the source branch 204. The source branch 204 transmits the light from the light source 202 to the optic coupler 206, which in turn delivers the light to the sample branch 208. The sample branch 208 then transmits the light to a scattering medium 214, which contains a plurality of scattering centers that reflect that light. The light reflected from the scattering centers, as well as light reflected from an end surface of the sample branch 208, travels back through the sample branch back to the coupler 206. At least a portion of that light is then delivered to the detector 212 via the detector branch 210.

The system 200 is capable of various specific configurations. In one such configuration, the light source 202 emits low-coherence light into a single-mode optical fiber 216 of the source branch 204. By way of example, the light source 202 comprises a broadband light source, such as a Hamamatsu Model #L3302, that produces light having a central wavelength of approximately 830 nm and a coherence length of approximately 5 μm to 20 μm, for instance 10 μm. In alternative embodiments, the light source can comprise an edge-emitting light emitting diode (LED), a superluminescent diode, multiple quantum well LEDs, a mode-locked Ti:AL203 laser, or a superfluorescent optical fiber. The light is transmitted through the single-mode optical fiber 216 and into a multi-mode optical waveguide 218, such as a multi-mode optical fiber, that is connected to the single-mode fiber optical with a coupler 220.

The optic coupler 206 is a 2×1 optic coupler and, in some configurations, comprises a graded index multi-mode coupler. Optionally, the sample branch 208 and the detector branch 210 comprise part of the optic coupler 206. In the system 200, both the sample branch 208 and the detector branch 210 comprise multi-mode optical waveguides, such as multi-mode optical fibers. By way of example, the detector 212 comprises a NewFocus Nirvana detector.

Figure 3:
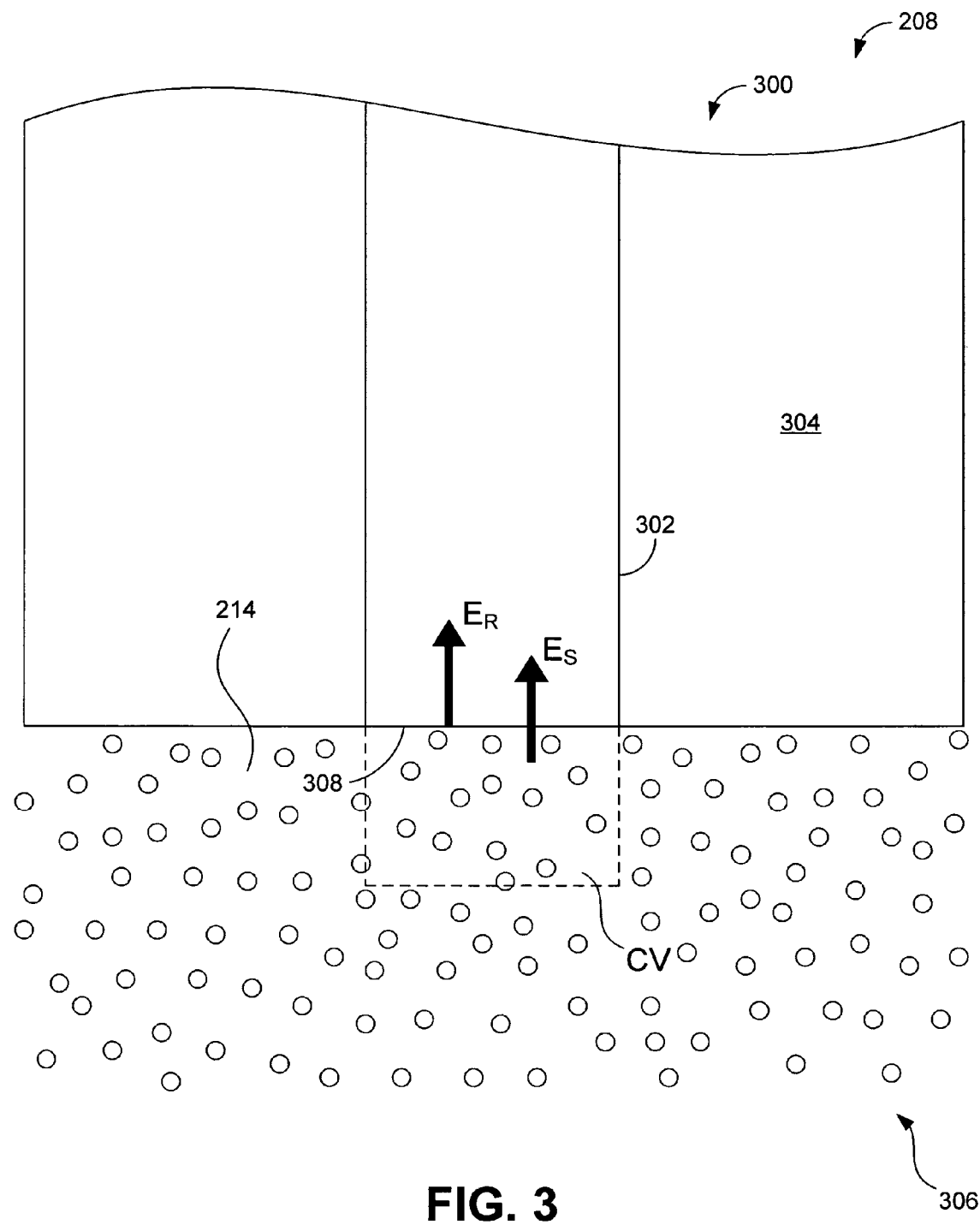
FIG. 3 illustrates an embodiment of a method for collecting light signals using a multi-mode optical waveguide.

FIG. 3 depicts the area adjacent an end of the sample branch 208 immersed in the scattering medium 214. By way of example, the scattering medium 214 comprises blood, which has both viscous and elastic properties (i.e., viscoelastic properties). Although blood has been specifically identified as an example fluid under evaluation, other fluids may be evaluated in similar manner. For example, the scattering medium can alternatively comprise colloidal dispersions or polymer solutions. As is illustrated in FIG. 3, the sample branch 208 comprises a multi-mode optical waveguide 300 that comprises an inner core 302 that is surrounded by an outer cladding 304. Although the core 302 of the multi-mode optical waveguide 300 comprises only a fraction of the total optical waveguide, the core is substantially larger, in terms of cross-sectional area, than the core of the single-mode optical fibers used in prior solutions (see FIG. 1). By way of example, the core 302 of the multi-mode optical waveguide 300 is approximately 40 μm to 50 μm in diameter, while the core of a single-mode optical fiber may be approximately 6 or 7 μm in diameter.

Light emitted from the light source 202 and delivered to the scattering medium 214 (FIG. 2) is reflected by scattering centers 306 suspended in the scattering medium within the coherence volume, CV, which is defined by the product of the coherence length of the light transmitted into the scattering medium and the cross-sectional area of the core 302. In instances in which the scattering medium 214 is blood, the scattering centers 306 may be red blood cells. By way of example, the depth of the coherence volume is approximately 5 μm to 20 μm, such that the volume is approximately 5 picoliters to 40 picoliters. By limiting that depth, the light reflected by scattering centers 306 beyond the coherence volume does not meet the coherence condition and therefore is not detected as an interference signal. The sampled light reflected by the scattering centers 306 within the coherence volume is represented by ES. In addition, reference light, in the form of Fresnel reflection, reflects back from the fiber-medium interface at an end surface 308 of the multi-mode optical waveguide core 302. The reflected light is represented by $E_R$. The reflected light amplifies the backscattering signal, which significantly increases the sensitivity of the technique.

With the increased cross-sectional area of the multi-mode optical waveguide core 302, rays are collected by a greater number of scattering centers 306 such that a greater collection efficiency is achieved and a higher signal-to-noise ratio is obtained at the detector 212 (FIG. 2). Significantly, that greater collection efficiency is not accompanied by a substantial increase in multiple scattering given that the depth of the fluid under observation, equivalent to the coherence length of the source light, is not increased. Therefore, the backscattered light undergoes on average only one scattering event in the coherence volume, thereby enabling a Gaussian assumption and indicating that the extracted information reflects the true properties of the scattering medium 214.

When the light in the single-mode optical fiber 216 is launched into the coupler 220 (FIG. 2), only the first modes of the multi-mode optical waveguide 218 are excited. Because small mode coupling is introduced by the coupler 220, most of the power is carried by the fundamental mode $U_1(r,\omega)$ and the incident field is well approximated by the relation:

$$E(r,\omega,L) = \sqrt{P_T} U_1(r,\omega) \exp(i\beta_1 L) \qquad \text{[Equation 4]}$$

where $P_T$ is the total input power, $\beta_1$ is the propagation constant of the eigenmode $U_1$, and L is the propagation distance between the source and the medium under evaluation.

The reference field $E_R(r,\omega,z)$ is obtained from the reflection of $E(r,\omega,L)$ at the end surface of the fiber 300. Due to the change of the propagation angle after the Fresnel reflection, a strong mode coupling occurs. The reference field is therefore a superposition of eigenmodes $U_m(r,\omega)$ and can be expressed as $$E_R(r,\omega,z) = \sqrt{P_T} \sum_{m=1}^{N} \sigma_{1m} U_m(r,\omega) \exp(i\beta_m z + i\beta_1 L) \qquad \text{[Equation 5]}$$

where $\beta_m$ is the propagation constant of mode $U_m$, $\sigma_{1m}$ is the coupling efficiency from mode $U_1$ to mode $U_m$ and N is the total number of propagating modes in the multimode fiber. One can notice from Equation 5 that all the mode are phase matched at z=0.

The portion $R_f P_T$ of the total power in the reference field is obtained by integrating $E_R(r,\omega,z)$ over the fiber surface as follows $$R_f P_T = \int |E_R(r,\omega,z)|^2 d^2 r \qquad \text{[Equation 6]}$$

Using Equation 5, Equation 6 becomes $$R_f P_T = P_T \int \sum_{m,n} \sigma_{1m}^* \sigma_{1n} U_m^*(r,\omega) U_n(r,\omega) \exp(i\beta_n z - i\beta_n z) d^2 r \qquad \text{[Equation 7]}$$

Since the eigenmodes $U_n$ of the fiber are orthonormal and satisfies the relation $$\int U_m^*(r,\omega) U_n(r,\omega) d^2 r = \delta_{nm} \qquad \text{[Equation 8]}$$

equation 7 simplifies to $$R_f P_T = P_{Tm} |\sigma_{1m}|^2 \qquad \text{[Equation 9]}$$

Assuming the power is evenly coupled in all the modes then $\sigma_{1m} = \sigma$ and $$|\sigma|^2 = \frac{R_f}{N} \qquad \text{[Equation 10]}$$

the non-reflected part of the incident field exits the fiber 300 and follows an optical path s in the medium. The part of the scattered light coupled back in the fiber 300 into the mode $U_n$ is characterized by the coefficient $\gamma_n$. The scattered field can then be written as a superposition of all the modes:

$$E_s(r,\omega,z,s) = \sqrt{P_T} \sum_n \gamma_n U_n(r,\omega) \exp\left(i\beta_n z + i\beta_1 L + i\frac{\omega}{c} s\right) \qquad \text{[Equation 11]}$$

The portion of the power coming back in the fiber 300 after diffusion in the medium is determined by the coupling efficiency C. The power launched into the medium being $P_T(1-R_f)$, it follows from Equation 11 that we have the relation $$C P_T (1 - R_f) = P_{Tn} |\gamma_n|^2 \qquad \text{[Equation 12]}$$

Assuming that all the modes are equally excited, $\gamma_n$ is independent of n and we deduce that $$|\gamma|^2 = \frac{C(1 - R_f)}{N} \qquad \text{[Equation 13]}$$

The frequency modulation of the intensity measured by the detector 212 arises from the interference between the reference field and the field scattered by the medium's flow. This modulated intensity is given by the real part of $$I_{RS} = \int S(\omega) \int E^*_R(r,\omega,z) E_s(r,\omega,z,s) d^2 r d\omega \qquad \text{[Equation 14]}$$

where $S(\omega)$ is the spectrum of the source. Using Equations 5 and 11, Equation 14 can be expressed as $$I_{RS} = \qquad \text{[Equation 15]}$$
$$\int S(\omega) \int \sqrt{P_T}_m \sigma^*_{1m} U^*_m(r,\omega) \exp(-i\beta_m z - i\beta_l L) \times \sqrt{P_T}_n$$
$$\gamma_{1n} U_n(r,\omega) \exp\left(i\beta_n z + i\beta_l L + i\frac{\omega}{c} s\right) d^2 r d\omega$$

Using the orthogonal property of the modes, Equation 15 simplifies to $$I_{RS} = P_{Tm} \int S(\omega) \sigma^*_{1m} \gamma_{1m} \exp\left(i\frac{\omega}{c} s\right) d\omega \qquad \text{[Equation 16]}$$

One can see from this last relation, that the different propagation constants $\beta_n$ of the modes are canceled and therefore do not introduce intermodal dispersion, which can reduce the detection efficiency. Most of the power coupled from the single mode optical fiber 216 to the multi-mode fiber 218 is indeed concentrated in the fundamental mode and almost no mode coupling occurs during the propagation to the scattering medium. At the fiber-medium interface, the modes are excited in phase and contribute constructively to the interference signal. Assuming that the coupling coefficients $\sigma_{1m}$ and $\gamma_{1m}$ are independent of $\omega$ and the mode number m, then, using Equations 10 and 13, Equation 16 can be expressed as $$I_{RS} = P_T \sqrt{C(1-R_f)R_f} \times \Gamma(S) \qquad \text{[Equation 17]}$$

where the self-coherence function $\Gamma(s)$ is defined as $$\Gamma(s) = \int S(\omega) \exp\left(i\frac{\omega}{c} s\right) d\omega \qquad \text{[Equation 18]}$$

When a single-mode coupler is used instead of multi-mode fiber, the modulated intensity has an expression similar to Equation 17, namely $$I_{RS} = P_T \sqrt{C_{SM}(1-R_f)R_f} \times \Gamma(S) \qquad \text{[Equation 19]}$$

where C has been replaced by the power coupling efficiency $C_{SM}$ of the single mode fiber. Due to their larger cores and numerical apertures, multi-mode optical waveguides have a much higher coupling efficiency than single-mode fibers, resulting in larger amplitude of the detected signal.

Figure 4:
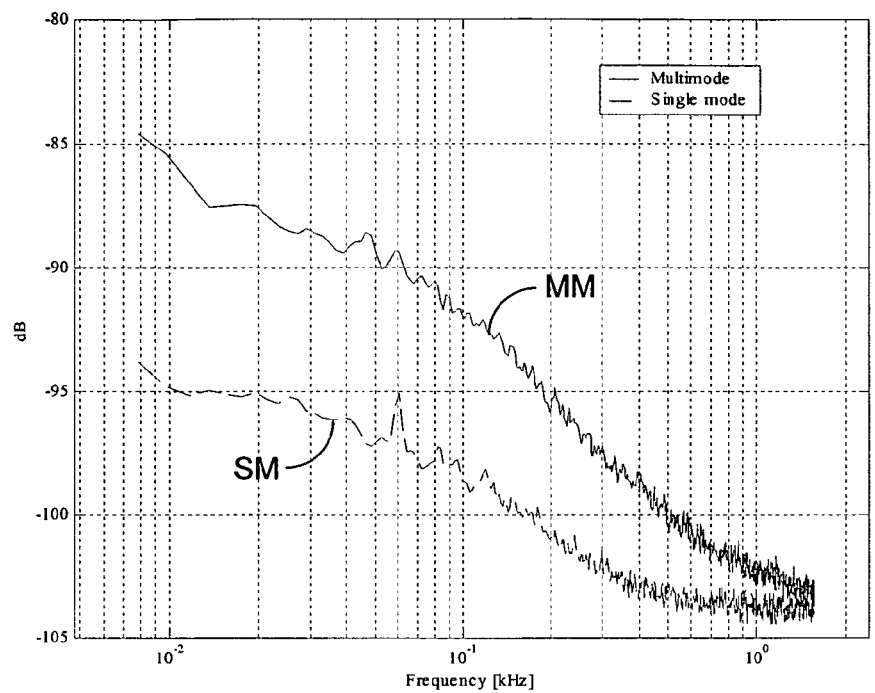
FIG. 4 is a graph that compares the strength of a single-mode signal to the strength of a multi-mode signal as a function of interference frequency.

The improvement to signal amplitude and signal-to-noise ratio when a multi-mode optical waveguide is used instead of a single-mode optical fiber is evident in the graph of FIG. 4. In that graph, illustrated are experimentally-observed intensity measurements in decibels (dB) relative to frequency (kHz) of the interference between the scattering centers and the reference reflection for single-mode (SM) optical fiber and multi-mode (MM) optical waveguide. As can be seen from FIG. 4, the signal in decibels is much larger for the multi-mode optical waveguide. In addition, the multi-mode plot does not flatten as does the single-mode plot, indicating that the multi-mode signal does is not impacted by the noise floor as is the single-mode signal.

Figure 5:
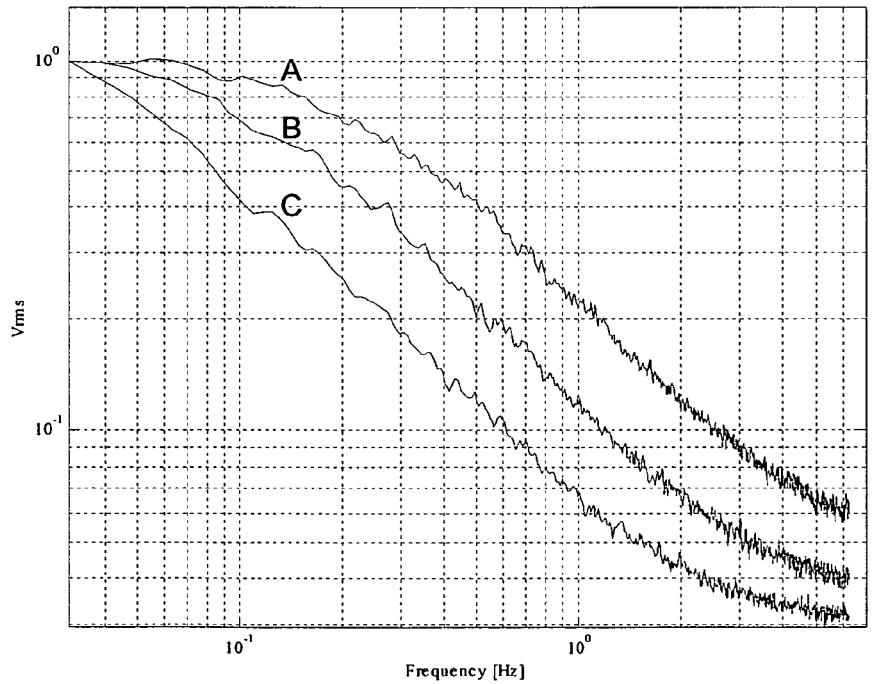
FIG. 5 is a graph that plots signal strength as a function of interference frequency for various particle sizes.

Referring to FIG. 5, illustrated are the results of dynamic measurements made in performing multi-mode, common-path interferometry consistent with the above-described methodology. More particularly, FIG. 5 provides plots of signal strength (measured in the voltage ($V_{rms}$) of the observed signal) for colloidal suspensions of microspheres of three different sizes: 200 nm (A), 359 nm (B), and 1,500 nm (C). Those plots reveal that the sensitivity of the signal to the size of the particle and indicates that a high signal-to-noise ratio is achieved for each particle size.

Figure 6:
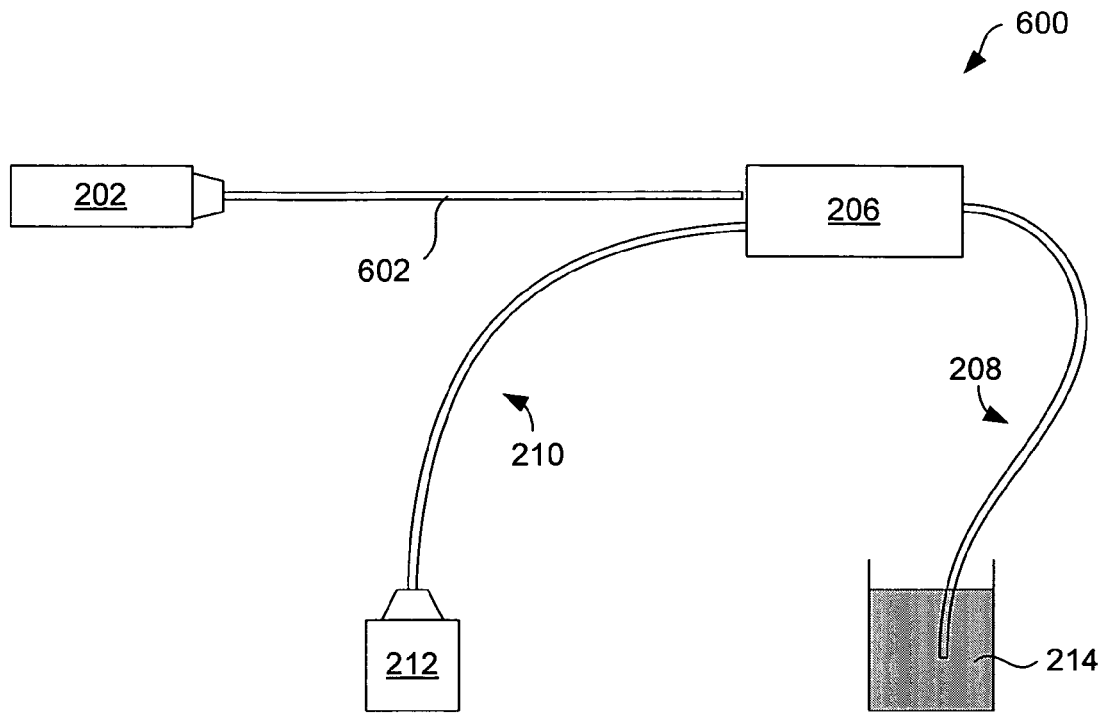
FIG. 6 illustrates a second embodiment of a light scattering sensing system.

FIG. 6 illustrates a second embodiment of a light scattering, sensing system 600. The system 600 shares several similarities with the system 200 illustrated in FIG. 2. Accordingly, the system 600 comprises a light source 202, an optic coupler 206, a sample branch 208 immersed in a scattering medium 214, a detector branch 210, and a detector 212. In the embodiment of FIG. 6, however, the source branch 602 comprises a multi-mode fiber, as opposed to a single-mode optical fiber that is coupled to a multi-mode optical waveguide.

Figure 7:
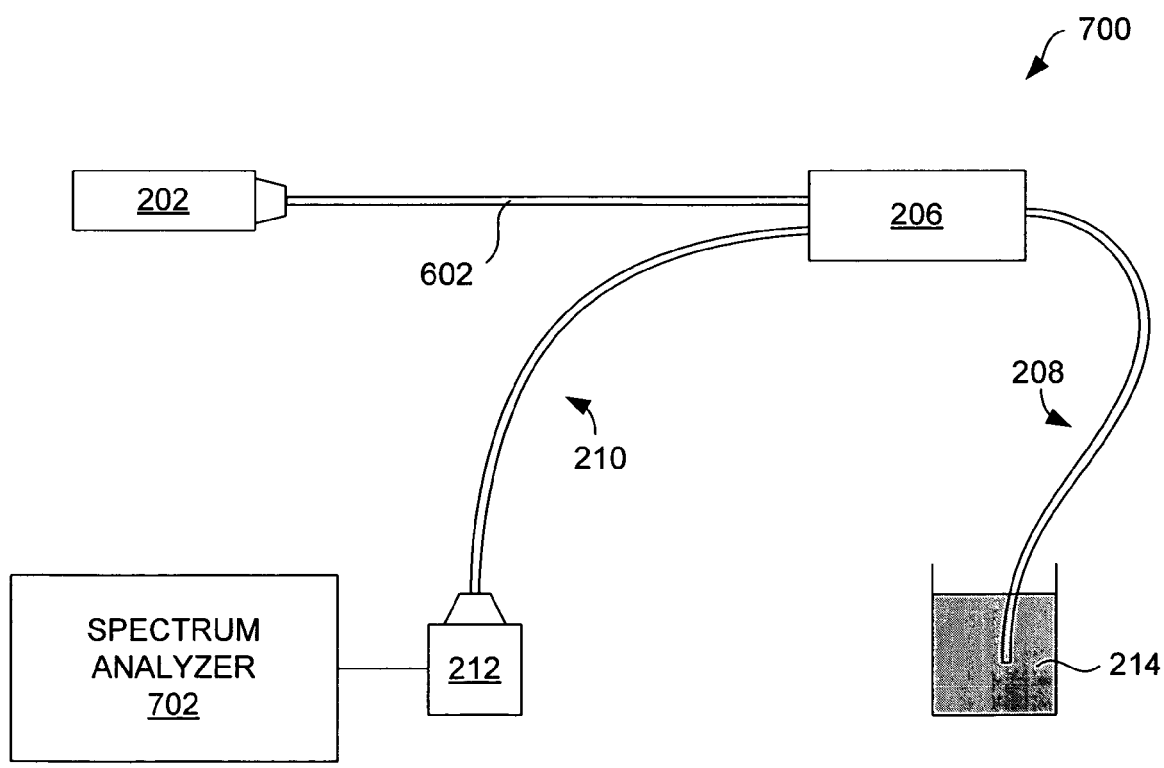
FIG. 7 illustrates a third embodiment of a light scattering sensing system.

FIG. 7 illustrates a third embodiment of a light scattering sensing system 700. Like the system of FIG. 6, the system comprises a light source 202, a source branch 602, an optic coupler 206, a sample branch 208 immersed in a scattering medium 214, a detector branch 210, and a detector 212. In the embodiment of FIG. 7, however, the detector 212 is coupled to a spectrum analyzer 702 that analyzes the detected signals in the frequency domain. By way of example, the spectrum analyzer 702 comprises a Stanford Research frequency spectrum analyzer, such as Model SR760.

Figure 8:
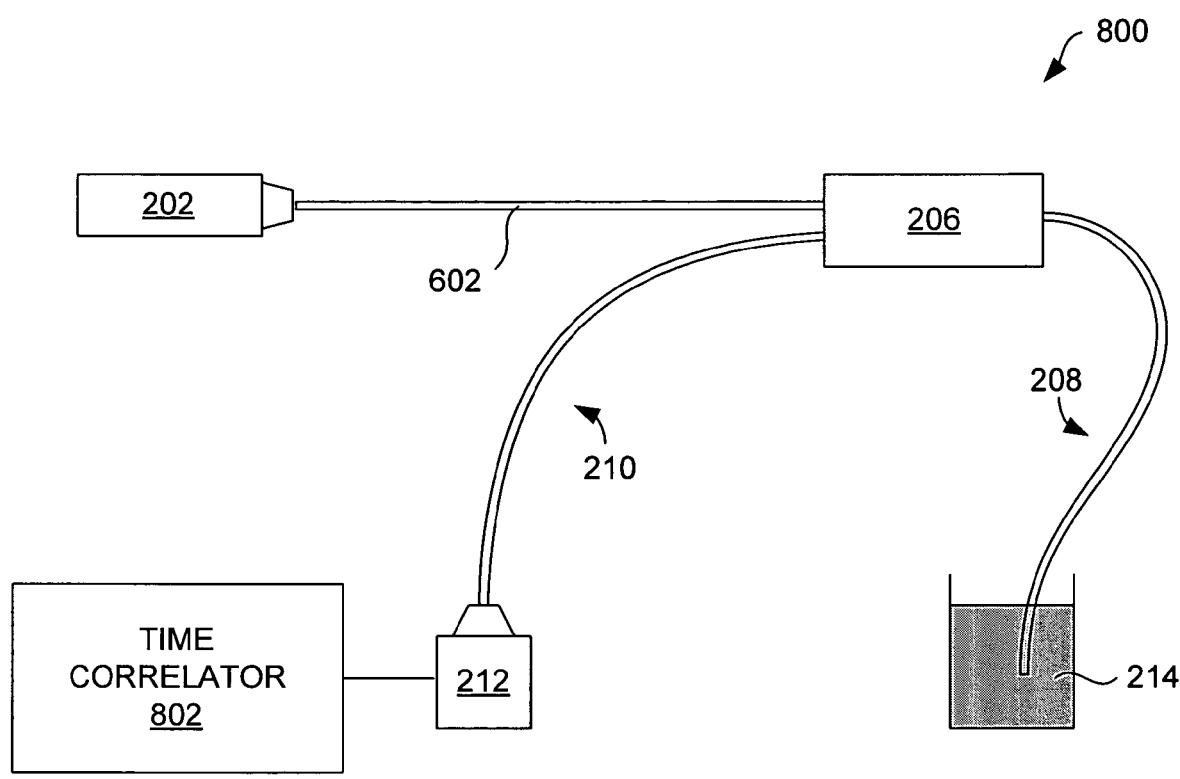
FIG. 8 illustrates a fourth embodiment of a light scattering sensing system.

FIG. 8 illustrates a fourth embodiment of a light scattering sensing system 800. Like the systems of FIGS. 6 and 7, the system comprises a light source 202, a source branch 602, an optic coupler 206, a sample branch 208 immersed in a scattering medium 214, a detector branch 210, and a detector 212. In the embodiment of FIG. 8, however, the detector 212 is coupled to a time correlator 802 that analyzes the detected signals in the time domain to obtain the temporal autocorrelation function of the fluctuating signal. By way of example, the time correlator 802 comprises a Brookhaven time correlation detector. Notably, because a strict relationship exists between the time and frequency domains, which may be determined by Fourier transformation, the analysis can be performed in the time domain using data provided by the time correlator 802.

Other embodiments for the light scattering sensing system are possible. Example alternative embodiments can include features described in U.S. Pat. No. 6,958,816, which is hereby incorporated by reference into the present disclosure. For instance, the system could be arranged to incorporate one or more reference mirrors, as in the embodiment shown in FIG. 9 of that patent, or to comprise an open-air configuration as in the embodiments shown in FIGS. 10 and 11 of that patent.

While the above-described embodiments have been described to identify example implementations of the disclosed systems and methods, other embodiments are feasible. For example, in some embodiments, one or more of the light source, detector, analyzer, and optical waveguide(s) can be integrated together in a single device. Such an integrated device may be of particular interest for evaluating colloidal or polymer solutions.

The invention claimed is:

1. A light scattering sensing system for analyzing a fluid, the system comprising:
   a low-coherence source of light;
   a sample branch comprising only one multi-mode optical waveguide configured to be placed within a fluid that contains a plurality of scattering centers that are suspended in the fluid and to transmit light generated by the low-coherence source of light to the fluid, the multi-mode optical waveguide further being configured to transmit light backscattered by the scattering centers and reflected from an end surface of the multi-mode optical waveguide;

a detector configured to detect the light signals transmitted by the sample branch; and a spectrum analyzer that analyzes detected signals in the frequency domain or a time correlator that analyzes detected signals in the time domain that enables mechanical properties of the fluid to be determined.

2. The system of claim 1, wherein the multi-mode optical waveguide comprises an inner core having a diameter ranging of approximately 40 μm to 50 μm.

3. The system of claim 1, wherein the source of low-coherence light emits light having a coherence length of approximately 5 μm to 20 μm.

4. The system of claim 1, wherein the multi-mode optical waveguide is configured to be placed within a flowing fluid that contains a plurality of scattering centers that are carried by the fluid as it flows.

5. A light scattering sensing system, comprising:

a source of low-coherence light;

a source branch that transmits light emitted by the source of low-coherence light;

a sample branch comprising a multi-mode optical waveguide configured to be placed within a fluid that contains a plurality of scattering centers and to transmit light received from the source branch to the fluid, the sample branch further being configured to transmit light backscattered by the scattering centers and reflected from an end surface of the multi-mode optical waveguide;

a detector branch configured to transmit the backscattered signals and the reflected signals received from the sample branch;

a coupler that couples at least two of the source branch, the sample branch, and the detector branch;

a detector configured to detect the signals transmitted by the detector branch; and a spectrum analyzer that analyzes detected signals in the frequency domain or a time correlator that analyzes detected signals in the time domain that enables mechanical properties of the fluid to be determined.

6. The system of claim 5, wherein the multi-mode optical waveguide comprises an inner core having a diameter of approximately 40 μm to 50 μm.

7. The system of claim 5, wherein the source of low-coherence light emits light having a coherence length of approximately 5 μm to 20 μm.

8. The system of claim 5, wherein the multi-mode optical waveguide is configured to be placed within a flowing fluid that contains a plurality of scattering centers that are carried by the fluid as it flows.

9. A method comprising:

radiating low-coherence light into a fluid using only one multi-mode optical waveguide;

collecting light signals backscattered by scattering centers suspended in the fluid and light reflected by an end surface of the multi-mode optical waveguide using the multi-mode optical waveguide; and determining mechanical properties of the fluid from the collected light signals.

10. The method of claim 9, wherein the multi-mode optical waveguide comprises an inner core having a diameter of approximately 40 μm to 50 μm.

11. The method of claim 9, wherein radiating low-coherence light comprises radiating light having a coherence length of approximately 5 μm to 20 μm.

12. The method of claim 9, wherein the scattering centers are contained in a coherence volume of approximately 5 picoliters to 40 picoliters.

13. The method of claim 9, wherein determining mechanical properties comprises analyzing the backscattered light signals and the reflected light signals using a spectrum analyzer that analyzes detected signals in a frequency domain.

14. The method of claim 9, wherein determining mechanical properties comprises analyzing the backscattered light signals and the reflected light signals using a time correlator that analyzes detected signals in a time domain.

15. The method of claim 9, wherein the fluid comprises blood.

16. The method of claim 15, wherein the scattering centers comprise red blood cells.

17. The method of claim 9, wherein determining the mechanical properties comprise determining at least one of one of elasticity, viscosity, or viscoelasticity.

18. The method of claim 9, wherein collecting light signals comprises collecting light signals backscattered by scattering centers being carried by a flowing fluid.

* * * * *